US009050423B2

(12) United States Patent
Peethambaran

(10) Patent No.: US 9,050,423 B2
(45) Date of Patent: Jun. 9, 2015

(54) MEDICAL NON REUSABLE SYRINGES

(75) Inventor: Baby Manoj Pournamil Peethambaran, Kerala (IN)

(73) Assignee: Baby Manoj Pournamil Peethambaran, Kerala (IN)

( * ) Notice: Subject to any disclaimer, the term of this patent is extended or adjusted under 35 U.S.C. 154(b) by 0 days.

(21) Appl. No.: 13/384,582

(22) PCT Filed: Jul. 14, 2010

(86) PCT No.: PCT/IN2010/000472
§ 371 (c)(1),
(2), (4) Date: Jan. 17, 2012

(87) PCT Pub. No.: WO2011/024188
PCT Pub. Date: Mar. 3, 2011

(65) Prior Publication Data
US 2012/0123333 A1    May 17, 2012

(30) Foreign Application Priority Data
Jul. 23, 2009   (IN) ............................ 1733/CHE/2009

(51) Int. Cl.
*A61M 5/00*   (2006.01)
*A61M 5/50*   (2006.01)
*A61M 5/32*   (2006.01)

(52) U.S. Cl.
CPC ....... *A61M 5/502* (2013.01); *A61M 2005/3279* (2013.01); *A61M 2005/5006* (2013.01)

(58) Field of Classification Search
CPC .............. A61M 5/502; A61M 5/3278; A61M 2005/3279; A61M 2005/5006
USPC ........................................................ 604/110
See application file for complete search history.

(56) References Cited

U.S. PATENT DOCUMENTS 3,320,954 A * 5/1967 Cowley .......................... 604/110
4,026,287 A * 5/1977 Haller ............................ 604/110
2006/0264826 A1  11/2006 Chen

FOREIGN PATENT DOCUMENTS

| CN | 1065021 A | 10/1992 |
| CN | 2500317 | 7/2002 |
| CN | 2542270 Y | 4/2003 |
| WO | WO 02/078773 A1 | 10/2002 |

OTHER PUBLICATIONS

International Search Report, Jan. 31, 2011, from International Phase of the instant application.

* cited by examiner

*Primary Examiner* — Laura Bouchelle
(74) *Attorney, Agent, or Firm* — Procopio, Cory, Hargreaves & Savitch LLP

(57) ABSTRACT

The invention is a single use syringe having an integrated mechanism to prevent its reuse, by manual intentional destruction after use, by an easy move. This prevents the reuse of syringes which may result in disease transmission if it is contaminated. It prevents auto destruction at an unwanted period so that it can be used for multiple purposes like blood aspiration and injection for a single patient and then dispose it as the medical staff stop attending that individual, thus saving valuable resources and generating less plastic waste. The manufacturing process is simple and brings not much added cost or special training for operation. The step for destruction is simple and quick without the aid of any special equipment, additional staff or electricity.

9 Claims, 3 Drawing Sheets

MEDICAL NON REUSABLE SYRINGES

The non reusable syringe is a new hot topic in medical field as these are expected to reduce transmission of many fatal diseases. But integrating the quality of non reusability to the syringes is continuing as a challenge. Most designs patented are complex in structure and are costly. Few of them needs special training to operate. The simpler ones are easily damageable and may fail during the operation. The current invention is an attempt to reduce the complexity and to prolong the functional capability to a reasonable length of time for proper operation.

FIELD OF INVENTION

Medical profession is standing helpless in front of fatal viral diseases like HIV and hepatitis. These are mostly transmitted by homo or heterosexual contact. But there are those people who become the innocent victims for these fatal diseases by the usage of blood products and contaminated instruments. Another group is intravenous drug addicts who secure illegal drugs from illegal sources and share syringes for drug administration; but for these people securing a syringe of their choice is possible through the same illegal source. So making good awareness and supplying safer syringes with non reusable quality integrated into them is the way to prevent disease transmission if illicit drug transport and trade is not that easy to eradicate.

The re usage of disposable syringes has been identified as a major cause for transmission of diseases between individuals by most of the health care agencies; and is identified as an easily preventable cause for disease transmission.

The WHO, UNICEF, UNFPA and many governmental and non governmental agencies across the world has started taking measures to block this easily preventable mode of disease transmission.

Present invention is a medical non reusable syringe that can be used for multiple uses on a single patient in single sitting and destroyed after attending that patient by a simple inherent mechanism.

STATE OF THE ART IN THE FIELD

The current methods of preventing reuse of disposable syringes are
1—Using non reusable syringe-which get spoiled after single use
2—Using separate mechanism to destroy syringes after their usage Non reusable syringes are being promoted by most of the international and local government agencies as an effective mode of preventing disease transmission. And this mainly operates by destroying the piston or plunger of the syringe, which get damaged after single use.

Complex mechanisms of rendering the syringes non reusable are described in various patent write ups The non reusable syringes can be auto damageable syringes or it can be damaged voluntarily by a simple move.

But most of these mechanisms make syringes which are simple structures to complex structures which are costly and many need special mode of operation for proper use. And this needs special training.

The separate syringe destroyers are special instruments that cut syringes through its tip, rendering the syringe non reusable. But this is a separate machine and need separate time and action for destruction of used disposable syringes. In many busy hospitals this job is done by separate staff and this increases the need for work force as well as proper monitoring

OBJECT OF INVENTION

Reuse of disposable syringes carry a risk of transmission of diseases as the sterilization of these easily damageable materials is often incomplete for fear of loss of functional integrity of the unit. And they are not manufactured to the quality needed for reuse.

There is risk of transmission of diseases by contaminated syringes and is a preventable cause for disease transmission.

The many non reusable syringe models available are set to work for one withdrawal and one forward movement, beyond which it will not work . . . they may prevent disease transmission among intravenous drug abusers, but is a headache for common medical personnel; unless they have extremely skilled and expert hands. Any single patient if need to have blood withdrawal and IV and IM injections need many syringes resulting in wastage of valuable resources and more plastic waste to dispose.

So the hospital supply syringes must be adequate to perform multiple actions in a single sitting on the same patient and can be easily destroyed by the end of attending every single patient.

The syringe described fulfills the above qualities.

STATEMENT OF INVENTION

The invention is involved in creating an easily damageable area on the barrel of the syringe, which holds the piston or Plunger inside it. The barrel is the most critical portion of manufacturing and the act to render the syringe non reusable is primarily targeted on it.

The concept is to create a thin area along the circumference of the barrel on its outer surface near its middle or near its ends with longitudinal and circumferential buttressing close to this groove and is the hospital supply model recommended.

For over the counter model there will be additional teeth like mechanism arising from the inner surface of the barrel which snap to permit the passage of the plunger across it but prevents its return by a snap lock system. The special feature Of this snap lock system is that they are connected to the outer surface of the barrel through gills which are out pouching with corrugated surfaces. These allow free movement of the plunger and prevent the regurgitation of the fluid being injected by the syringe. This system allows smooth injection and ripping of the gills on attempting to pull back the plunger once it is fully pushed up the barrel

DETAILED DESCRIPTION WITH DRAWINGS

In order to facilitate better understanding of the invention a detailed description of the preferred embodiments of the present invention will now be explained with reference, to accompanying drawings. It should be understood that the discussed embodiments are merely exemplary to the invention, which may be embodied in various forms. Therefore the details disclosed herein are not to be interpreted limiting but merely as the basis for claims and as the basis for teaching one skilled in the art, how to make or use the invention.

DETAILED DESCRIPTION WITH DRAWINGS

The invention introduces two new properties to the disposable syringes to prevent their re usage.

The first property is a voluntary non reusable method where the medical personnel damage the syringe by a simple voluntary motion after its usage.

The second property is locking the syringe by the end of using the syringe, and any attempt to reuse the syringe will involuntarily damage the syringe to make it auto nonreusable.

Figure 1:
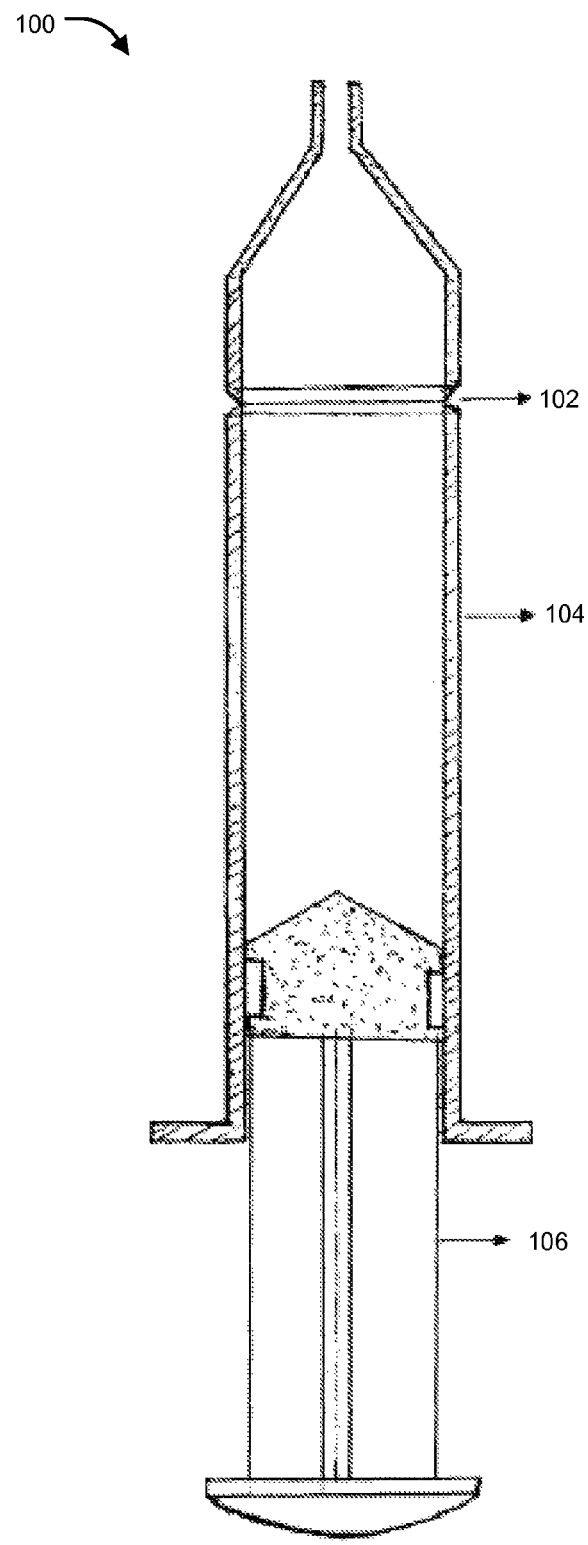
FIG. 1 represents a vertical elevation of a syringe with a circular groove marked as 102 along the outer surface of the barrel and is generally located towards the needle attaching end of the outer piece of the syringe. 104 represents the outer part and 106 represents the inner part of the syringe.
Figure 2:
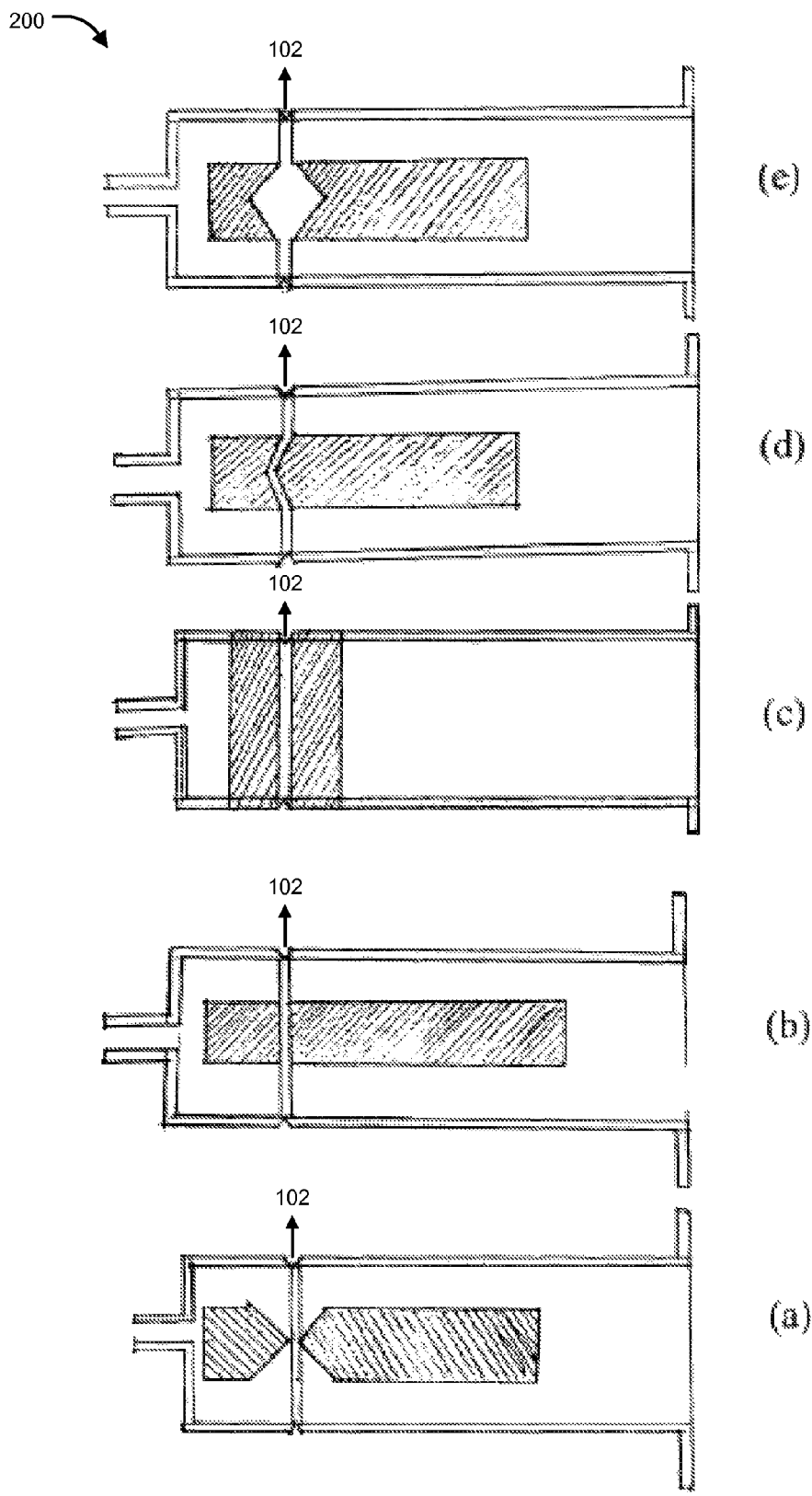
FIG. 2 is the image representing few examples of various types of buttressing possible; marked on the syringe as shaded area. They are placed to enhance the breakage of the thin area between them.

The FIG. 1 and FIG. 2 represent incorporation of the property of voluntary nonreusability to the syringe.

FIG. 1

This gives the image of vertical elevation of the outer part of the syringe. This part carries a focal rarified or thinned area on its outer aspect and is marked as "102". It is along this line the syringe breaks away on applying pressure

FIG. 2

Figure 3:
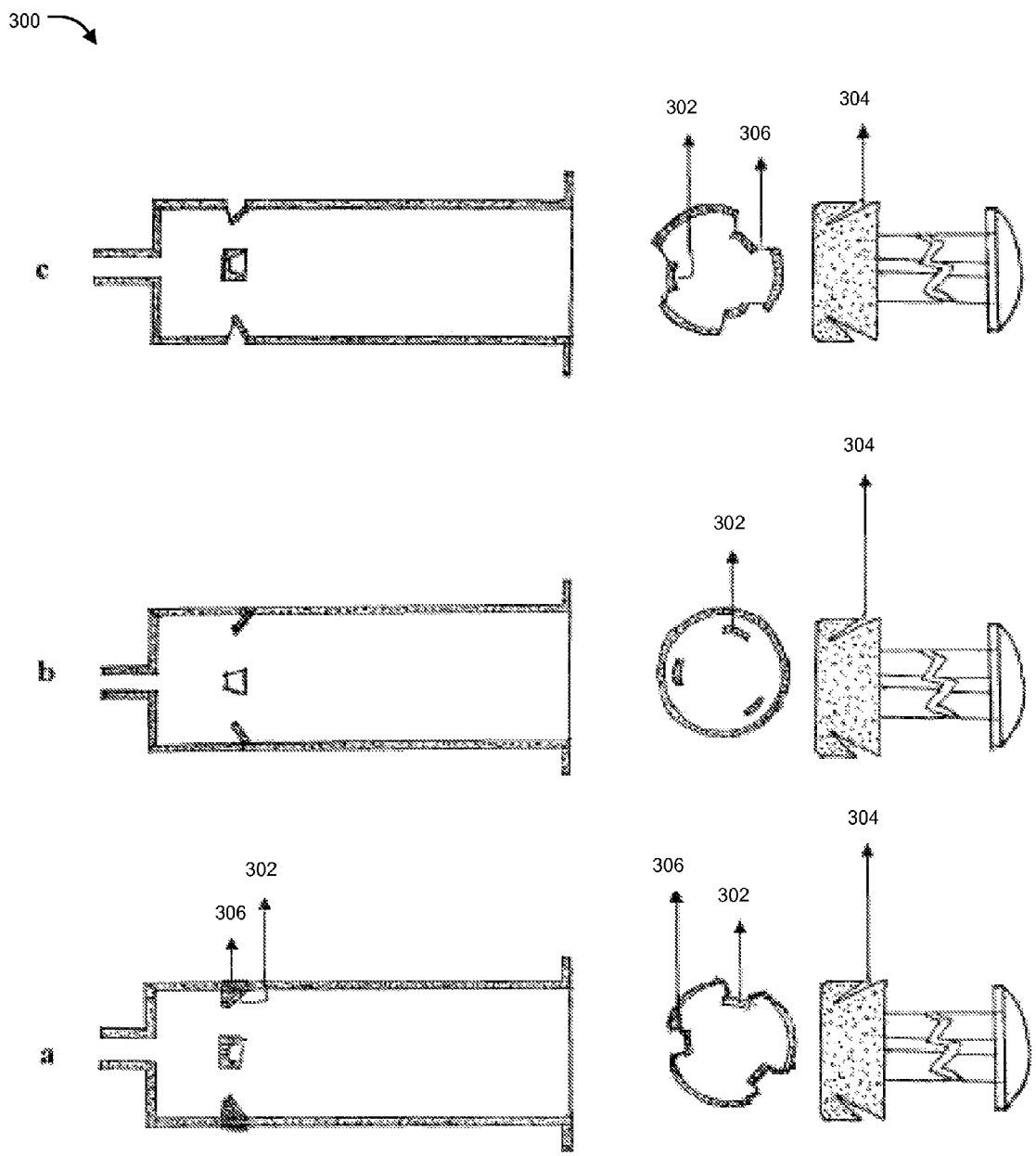
FIG. 3 is showing three different patterns of inner projections and their cross sectional images. The figure of syringe showing inner projection 302 and corrugated connection to the outer surface 306 with the groove 304 on the inner piece to trap the inner projection of outer piece is shown in FIG. "3a". The inner projection without corrugated connection is shown in FIG. "3b" and a thin elastic connection instead of corrugated connection in FIG. "3c". The corresponding cross sections at the level of inner projections and inner piece with its groove 304 to be locked with the inner projections is shown to the right.

This gives the images of various types of buttressing or thickenings on the outer aspect of the outer part of syringes so that the force applied along the buttressing tend to travel along them and make the thin area 102 represented in the FIG. 1 more liable to damage under pressure The FIG. 3 represents the property of involuntary non reusability to the syringe.

FIG. 3

This gives the image of the outer and inner piece of the syringe along with cross section through the locking mechanism. The FIG. "3a" shows the inner projection of any size that is projected from the inner aspect of the outer part of the syringe and is represented by the letter 302. From the outer and lateral aspect of these projections a corrugated membrane is connected to the outer aspect of the outer part of the syringe. The purpose of these connections is to allow the inner projections to yield outward permitting the inner part of the syringe to pass beyond them. The corresponding defect covered with the corrugated membrane on the same portion of the outer part of the syringe allows free accommodation of the inner projection with minimal or no regurgitation of fluid into the corrugated part or to the exterior.

Once the inner part is passed beyond the inner projection the inner projection comes back towards its normal position and gets locked to the groove 304 on the inner part of the syringe. Any attempt to pull back this inner piece will result in tearing apart of the thin corrugated portion 306. The FIG. "3b" represents another possible model where the inner projections 302 is simply projecting from the inner aspect of the syringe and will get locked to the groove 304 on the inner part of the syringe.

The FIG. "3c" represents another model where the corrugated membrane 306 is replaced by a thin elastic membrane. This thin elastic membrane functions for the corrugated membrane in a similar manner.

The above two properties can be incorporated to a syringe either alone or in a combined manner to render it non reusable depending on the demand at the end user.

The foregoing description of the preferred embodiments is provided to enable any person skilled in the art to make or use the present invention. The various modifications to these embodiments will be readily apparent to those skilled in the art, and the generic principles defined herein may be applied to other embodiments without the use of the inventive faculty. Thus the present invention is not intended to be limited to the embodiments shown herein but is to be accorded the widest scope consistent with the principles and novel features disclosed herein. Various changes and modifications may be made therein without departing from the spirit of the invention. Such changes and modifications are to be understood as included within the scope of the present invention as defined by the appended claims unless they depart there from

SCOPE OF INVENTION

The mechanism adopted in syringes can be extended to other disposable equipments which have hazardous consequences on re usage.

The invention claimed is:

1. A disposable syringe comprising
   a barrel portion and
   a plunger portion,
   wherein said barrel portion is configured to at least partially surround a circumference of the plunger portion, the barrel portion comprising a focal area of lower thickness on its outer aspect, and wherein said focal area is located near a needle attaching end of said syringe such that when manual pressure above a defined threshold is put on said focal area said syringe is capable of being broken, rendering the syringe non reusable.

2. The syringe according to claim 1, wherein one or more buttressing or thickening can be implemented on said outer aspect of said barrel, wherein force applied along said buttressing or thickening makes said focal area prone to damage under manual pressure above said defined threshold.

3. The syringe according to claim 1, wherein said focal area is formed along circumference of said barrel.

4. The syringe according to claim 2, wherein said focal area is located closer to needle attaching end, and wherein said buttressing comprises one or a combination of projections, elongations or caps to enhance ease of applying pressure to present spillage of blood or other fluid inside said syringe.

5. A disposable syringe comprising
   at least one inward projections of the syringe,
   a corrugated membrane coupled with a groove configured in the syringe, wherein said corrugated membrane is configured to enable said groove to hold said at least one inward projection when plunger of said syringe passes through said at least one inward projection,
   wherein when said plunger passes through said at least one inward projection, said at least one inward projection moves back to original position from within said corrugated membrane and locks said plunger preventing said plunger from moving back.

6. A disposable syringe comprising
   at least one inward projection of the syringe, and
   a thin elastic membrane coupled with a groove configured in the syringe, wherein said thin elastic membrane is configured to enable said groove to hold said at least one inward projection when plunger of said syringe passes through said at least one inward projection, wherein when said plunger passes through said at least one inward projection, said at least one inward projection moves back to original position from within said thin elastic membrane and locks said plunger preventing said plunger from moving back.

7. The syringe according to claim 5, wherein said corrugated membrane is operatively coupled with said groove to hold said at least one inward projection.

8. The syringe according to claim 5, wherein pulling the plunger backwards through said at least one inward projection causes stretching of said corrugated membrane and break off of said membrane rendering the syringe non reusable.

9. The syringe according to claim 5, wherein said syringe comprises said groove, and wherein said at least one inner projection locks onto said groove once said plunger passes through.

* * * * *